(12) United States Patent
Tanji

(10) Patent No.: US 9,289,126 B2
(45) Date of Patent: Mar. 22, 2016

(54) SUBJECT INFORMATION OBTAINING APPARATUS, SUBJECT INFORMATION OBTAINING METHOD, AND PROGRAM

(75) Inventor: Koichi Tanji, Kawasaki (JP)

(73) Assignee: CANON KABUSHIKI KAISHA, Tokyo (JP)

( * ) Notice: Subject to any disclaimer, the term of this patent is extended or adjusted under 35 U.S.C. 154(b) by 1036 days.

(21) Appl. No.: 12/975,423

(22) Filed: Dec. 22, 2010

(65) Prior Publication Data

US 2011/0178739 A1 Jul. 21, 2011

(30) Foreign Application Priority Data

Jan. 18, 2010 (JP) .................................. 2010-008366

(51) Int. Cl.
| | | |
|---|---|---|
| G06F 19/00 | (2011.01) | |
| A61B 5/00 | (2006.01) | |
| A61B 8/13 | (2006.01) | |
| G06T 11/00 | (2006.01) | |

(52) U.S. Cl.
CPC ............. *A61B 5/0059* (2013.01); *A61B 5/0095* (2013.01); *A61B 8/13* (2013.01); *G06T 11/006* (2013.01)

(58) Field of Classification Search
CPC .................................................... G06T 11/006
USPC ........................................... 702/56; 600/437
See application file for complete search history.

(56) References Cited

U.S. PATENT DOCUMENTS

2009/0002685 A1* 1/2009 Fukutani et al. ................. 356/72
2009/0198128 A1* 8/2009 Fukutani et al. .............. 600/437

FOREIGN PATENT DOCUMENTS

WO 2009/073979 6/2009

OTHER PUBLICATIONS

Paltauf et al. "Iterative reconstruction algorithm for optoacoustic imaging", Oct. 2002, J. Acoust. Soc. vol. 112, No. 4, p. 1536-1544.*
MH Xu et al., "Photoacoustic Imaging in Biomedicine", *Review of Scientific Instruments*, vol. 77 (2006), 22 pages.

(Continued)

*Primary Examiner* — Patrick Assouad
*Assistant Examiner* — Haidong Zhang
(74) *Attorney, Agent, or Firm* — Fitzpatrick, Cella, Harper & Scinto

(57) ABSTRACT

A subject information obtaining apparatus has: a light source; a plurality of receiving elements which receive acoustic waves generated from a subject, and output signals; a memory unit for storing, for each of a plurality of predetermined positions, information to represent signals which are output from the plurality of receiving elements when an acoustic wave source is assumed to exist in the position; and an estimating unit for estimating a distribution of acoustic wave sources. The estimating unit assumes a distribution of acoustic wave sources, obtains signals corresponding to positions of respective acoustic wave sources in the assumed distribution from the stored information, and defines a distribution of acoustic wave sources, of which degree of coincidence between the obtained signals and signals obtained in an actual measurement is highest, as the distribution of acoustic wave sources.

19 Claims, 14 Drawing Sheets

(56) References Cited

OTHER PUBLICATIONS

J Zhang et al., "Comparison of Iterative Reconstruction Approaches for Photoacoustic Tomography", *Proc. of SPIE*, vol. 6437 (2007), 6 pages.

J. Zhang et al., "Effects of Different Imaging Models on Least-Squares Image Reconstruction Accuracy in Photoacoustic Tomography", *IEEE Transactions on Medical Imaging*, vol. 28, No. 11, pp. 1781-1790 (Nov. 2009), XP012003092.

G. Paltauf et al., "Iterative Reconstruction Algorithm for Optoacoustic Imaging", *J. Acoust. Soc. Am.*, vol. 112, No. 4, pp. 1536-1544 (Oct. 2002), XP011283932.

\* cited by examiner

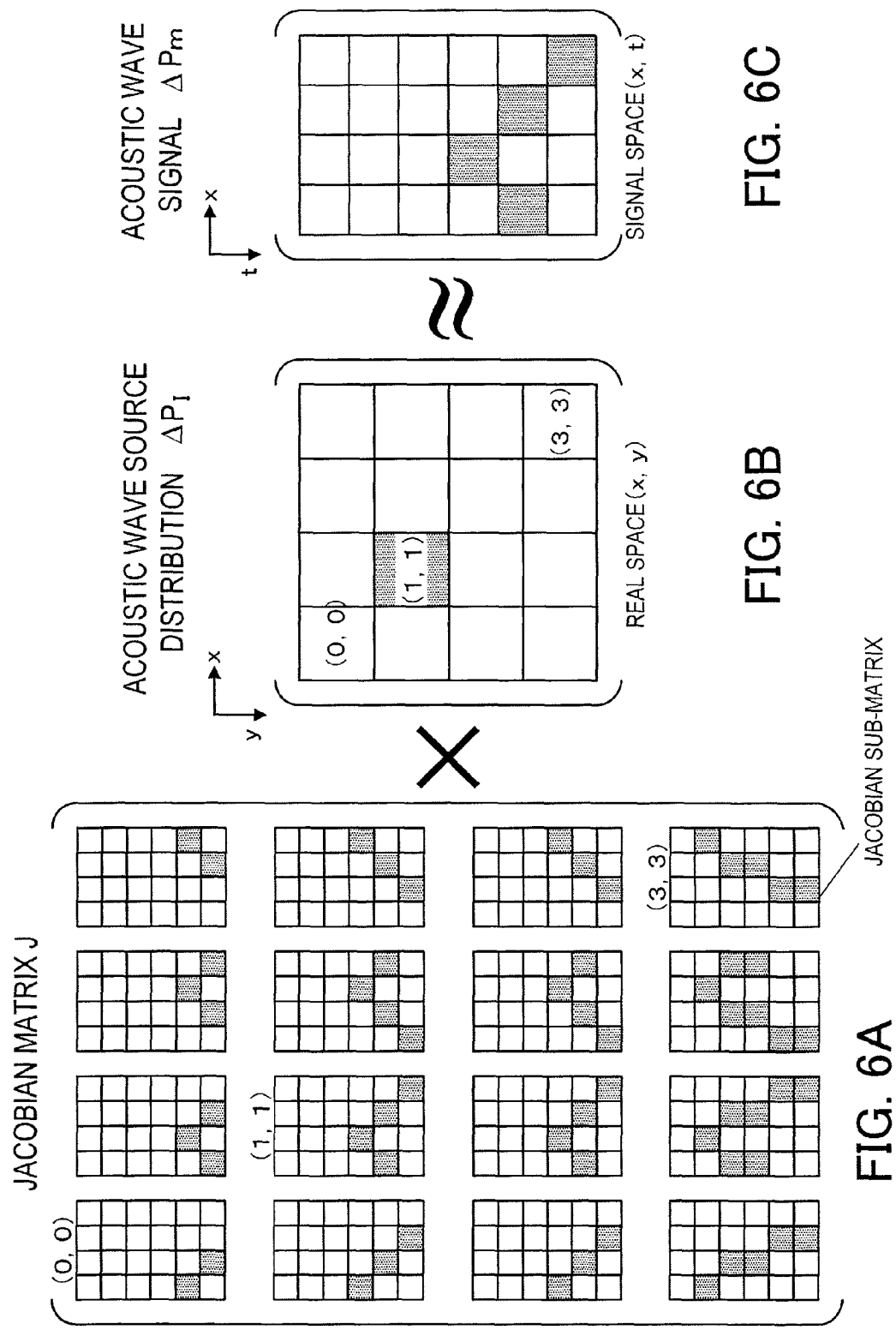

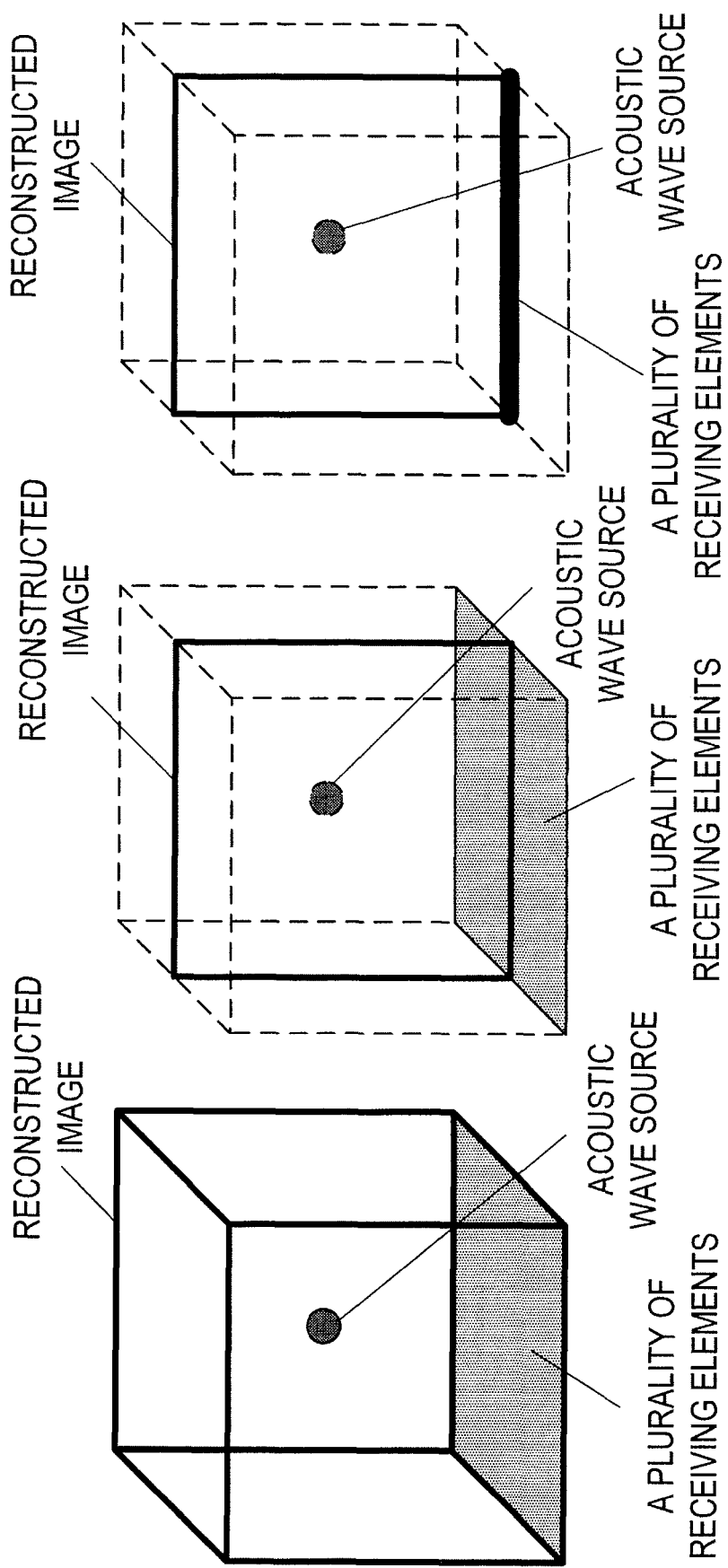

SUBJECT INFORMATION OBTAINING APPARATUS, SUBJECT INFORMATION OBTAINING METHOD, AND PROGRAM

BACKGROUND OF THE INVENTION

1. Field of the Invention

The present invention relates to a subject information obtaining apparatus, subject information obtaining method, and programs.

2. Description of the Related Art

In diagnosing breast cancer or the like, many biological information obtaining apparatuses using X-rays (mammography), acoustic waves and MRI (Magnetic Resonance Imaging) are used. Recently a biological information imaging apparatus, which propagates pulsed light in the biological tissue, detects acoustic waves (typically ultrasonic waves) generated by absorbing the propagating light on the surface of the biological tissue, and images the initial generation pressure distribution or light absorption coefficient distribution in the biological tissue, is receiving attention.

In order to obtain a light absorber in biological tissue, it is necessary to reconstruct an image using received signals on the acoustic waves. As an example of an image reconstruction method, a method for constructing an image by back projection of the signals (back projection method) is available. The back projection method is disclosed in Non-patent Literature 1 (NPL 1) "Photoacoustic imaging in biomedicine, REVIEW OF SCIENTIFIC INSTRUMENTS Vol. 77, 041101, (2006)".

Another example of the image reconstruction method is estimating acoustic wave sources iteratively, and determining a least square solution with the signal to construct an image (iteration method). The iteration method is disclosed in Non-Patent Literature 2 (NPL 2) "Comparison of iterative reconstruction approaches for photoacoustic tomography, Proc. of SPIE Vol. 6437 64370 (2007)".

SUMMARY OF THE INVENTION

According to NPL 1, in the case of an ordinary photoacoustic wave imaging apparatus, a biological information can be imaged perfectly by detecting the acoustic waves in all the positions (directions) on a surface of a closed sphere, on an infinite plane, or on a surface of a cylinder having infinite length.

However in the case of diagnosing a biological tissue, acoustic waves cannot be detected by such a method (acoustic waves cannot be detected in all the directions around the biological tissue). Therefore an acoustic wave detector is set on a part of the biological tissue to detect the acoustic waves. In this case, as the distance between a light absorber and the acoustic wave detector becomes longer, the solid angle formed by the acoustic wave detector and the light absorber decreases, and uncertainty of the obtained information (internal information of the biological tissue: information on distribution of the acoustic wave sources) increases.

If the uncertainty of the obtained information increases, a virtual image (artifact), which does not actually exist, is generated when the image is reconstructed by the back projection method according to NPL 1, for example. Resolution (lateral resolution) also decreases, which drops diagnostic accuracy.

According to the iteration method, on the other hand, it is reported that the generation of artifacts and the drop in lateral resolution can be suppressed even if the acoustic waves in all the directions around the biological tissue cannot be detected. However the processing load is high in the method disclosed in NPL 2, since acoustic waves are calculated using an analytic solution every time iterative calculation is performed. In this method, it is very inefficient to obtain actual measurement conditions, such as the size of the receiving element and the frequency band of acoustic waves that can be received every time iterative calculation is performed. Even in the case of calculating acoustic waves by performing simulation considering actual measurement conditions, calculation time and memory become enormous (reconstruction of a three-dimensional image is difficult).

It is an object of the present invention to provide a technology to accurately estimate a distribution of acoustic wave sources by a simple method when acoustic waves cannot be detected in all the directions around the subject.

A subject information obtaining apparatus, comprising:

a plurality of receiving elements which receive acoustic waves generated from a subject by irradiation of light, and output signals;

a memory unit for storing, for each of a plurality of predetermined positions, information to represent signals which are output from the plurality of receiving elements when an acoustic wave source is assumed to exist in the position; and an estimating unit for estimating a distribution of acoustic wave sources in the subject based on signals which are output from the plurality of receiving elements in an actual measurement and the information stored in the memory unit, wherein the estimating unit assumes a distribution of acoustic wave sources, obtains signals corresponding to positions of respective acoustic wave sources in the assumed distribution from the information stored in the memory unit, and defines a distribution of acoustic wave sources, of which degree of coincidence between the obtained signals and signals obtained in the actual measurement is highest, as the distribution of acoustic wave sources in the subject.

A subject information obtaining method for a subject information obtaining apparatus having a memory unit for storing, for each of a plurality of predetermined positions, information to represent signals which are obtained from a plurality of receiving elements when an acoustic wave source is assumed to exist in the position, comprising the steps of:

receiving acoustic waves generated in a subject by irradiation of light onto the subject, by the plurality of receiving elements, and generating signals; and estimating a distribution of acoustic wave sources in the subject based on signals obtained from the plurality of receiving elements in an actual measurement, and the information stored in the storage unit, wherein in the step of estimating a distribution of acoustic wave sources in the subject, a distribution of acoustic wave sources is assumed, signals corresponding to positions of respective acoustic wave sources in the assumed distribution are obtained from the information stored in the memory unit, and a distribution of acoustic wave sources, of which degree of coincidence between the obtained signals and signals obtained in the actual measurement is highest, is defined as the distribution of acoustic wave sources in the subject.

A program causing a computer to execute a step of estimating a distribution of acoustic wave sources in a subject based on signals which are output from a plurality of receiving elements by receiving, by the plurality of receiving elements, acoustic waves generated in the subject by irradiating light onto the subject in an actual measurement, and information which is stored in a memory unit and which represents, for each of a plurality of predetermined positions, signals to be output from the plurality of receiving elements when an acoustic wave source is assumed to exist in the position, wherein in the step of estimating a distribution of acoustic wave sources in the subject, a distribution of acoustic wave sources is assumed, signals corresponding to positions of respective acoustic wave sources in the assumed distribution are obtained from the information stored in the memory unit, the obtained signals are superposed, and a distribution of acoustic wave sources, of which degree of coincidence between the superposed signals and signals obtained in the actual measurement is highest, is defined as the distribution of acoustic wave sources in the subject.

A subject information obtaining apparatus, comprising:

a plurality of receiving elements which receive acoustic waves generated from a subject by irradiation of light, and output signals;

a memory unit for storing, for each of a plurality of predetermined positions, information to represent signals which are output from the plurality of receiving elements when an acoustic wave source is assumed to exist in the position; and an estimating unit for estimating a distribution of acoustic wave sources in the subject based on signals which are output from the plurality of receiving elements in an actual measurement and the information stored in the memory unit, wherein the estimating unit assumes a distribution of acoustic wave sources, obtains signals based on the assumed distribution and the information stored in the memory unit, and defines a distribution of acoustic wave sources, of which degree of coincidence between the obtained signals and signals obtained in the actual measurement is highest, as the distribution of acoustic wave sources in the subject.

A subject information obtaining method for a subject information obtaining apparatus having a memory unit for storing, for each of a plurality of predetermined positions, information to represent signals which are obtained from a plurality of receiving elements when an acoustic wave source is assumed to exist in the position, comprising the steps of:

receiving acoustic waves generated in a subject by irradiation of light onto the subject, by the plurality of receiving elements, and generating signals;

estimating a distribution of acoustic wave sources in the subject based on signals obtained from the plurality of receiving elements in an actual measurement, and the information stored in the memory unit, wherein in the step of estimating a distribution of acoustic wave sources in the subject, a distribution of acoustic wave sources is assumed, and a distribution of acoustic wave sources, of which degree of coincidence between signals obtained based on the assumed distribution and the information stored in the memory unit, and the signals obtained in the actual measurement is highest, is defined as the distribution of acoustic wave sources in the subject.

According to the present invention, a distribution of acoustic wave sources can be estimated accurately when acoustic waves cannot be detected in all the directions around a subject.

Further features of the present invention will become apparent from the following description of exemplary embodiments with reference to the attached drawings.

BRIEF DESCRIPTION OF THE DRAWINGS

FIG. 6A, FIG. 6B and FIG. 6C are diagrams depicting an example of equations used to estimate acoustic wave source distribution in matrix format;

FIG. 13A, FIG. 13B and FIG. 13C are diagrams depicting examples of an array pattern of a receiving element and obtained reconstructed image.

DESCRIPTION OF THE EMBODIMENTS

A biological information obtaining apparatus and a biological information obtaining method according to the present embodiment will now be described with reference to the drawings. The following embodiment is an example, and does not limit the present invention. In the present invention, an acoustic wave includes a sound wave, an ultrasonic wave and a photoacoustic wave, and is referred to as an "elastic wave" which is generated in a subject when such a light as near-infrared (electromagnetic wave) is irradiated onto the subject. In the following description, a biological information obtaining apparatus (biological information imaging apparatus), in which a biological tissue is used as a subject, is described, but the present invention is not limited to this. The present invention can also be implemented as a subject information obtaining apparatus, subject information obtaining method, and a program which can measure subjects other than biological tissue as well.

(Apparatus Configuration)

Figure 1:
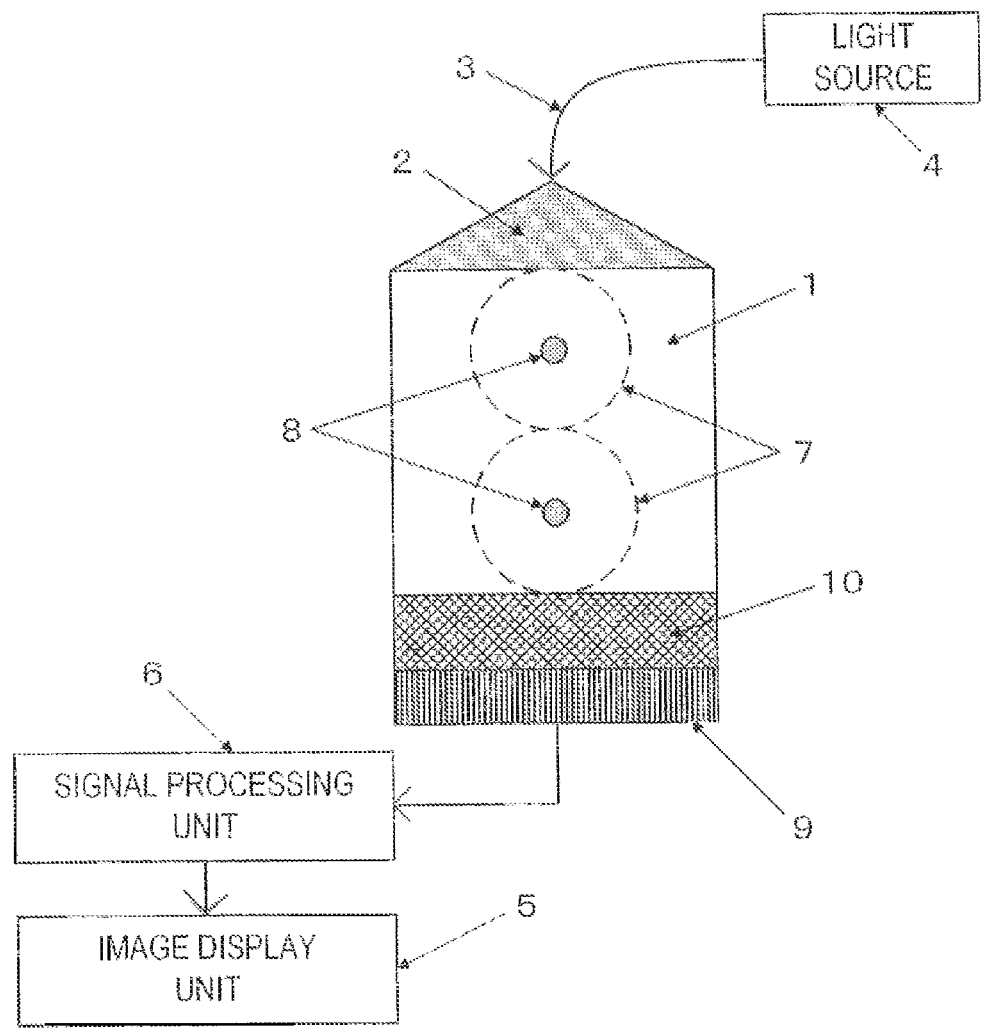
FIG. 1 is a diagram depicting an example of a configuration of a biological information imaging apparatus according to the present embodiment.

Initially an overview of a biological information obtaining apparatus according to the present embodiment will be described. As an example of the biological information obtaining apparatus, a biological information imaging apparatus, which estimates distribution of an acoustic wave source in a biological tissue and generates an image, will be described. FIG. 1 shows an example of the configuration of the biological information imaging apparatus according to the present embodiment.

The biological information imaging apparatus according to the present embodiment has a light source 4 which irradiates pulsed light 2 onto a biological tissue 1, which is a subject. Normally the pulsed light 2 emitted from the light source 4 is irradiated onto the surface of the biological tissue 1 via a light propagation apparatus 3, such as an optical fiber and liquid light-guide.

The biological information imaging apparatus according to the present embodiment further has a plurality of receiving elements (acoustic wave detectors 9) which receive an acoustic wave generated by light absorption and output signals. In concrete terms, the plurality of receiving elements detect an acoustic wave 7 which is generated by a light absorber 8 in the biological tissue 1 absorbing a part of the energy of the light, and convert the acoustic wave 7 into electric signals. It is preferable that the plurality of receiving elements are disposed in a two-dimensional array. In the front portion (biological tissue 1 side) of each acoustic wave detector 9, a pressing plate 10, for firmly securing the subject, is disposed.

The biological information imaging apparatus according to the present embodiment further has a signal processing unit 6 which analyzes an electric signal obtained by the acoustic wave detector 9, and an image display unit 5 which displays an image (reconstructed image) based on the processing signal.

In concrete terms, the signal processing unit 6 has an information generating unit, memory unit and estimating unit. The information generating unit generates information to be stored in the memory unit by numerical analysis. The memory unit stores information to indicate signals to be output from the plurality of receiving elements, for each of a plurality of predetermined positions respectively, when an acoustic wave source is assumed to exist in the position. The estimating unit estimates the distribution of the acoustic wave sources (acoustic wave source distribution) in a biological tissue, based on signals which are output from the plurality of receiving elements in an actual measurement and the information stored in the memory unit.

The image display unit 5 is an image display apparatus, such as a liquid crystal display, plasma display, organic EL display and a display having an electron-emitting device.

Figure 3:
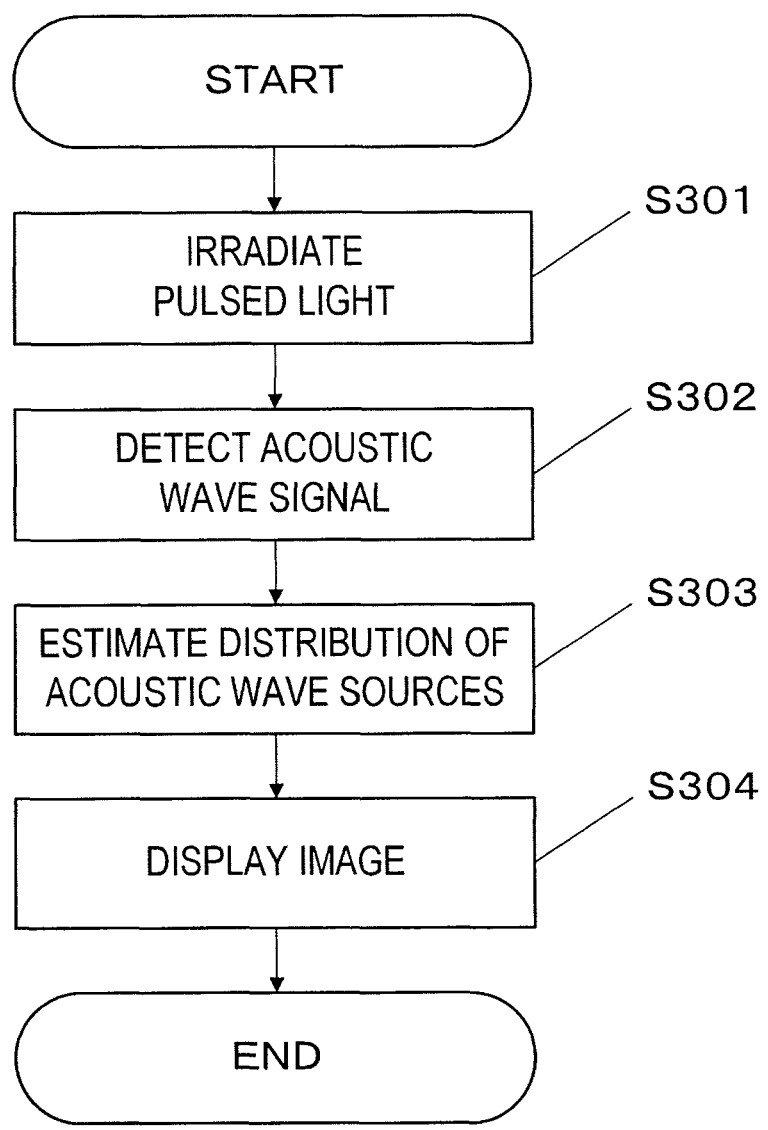
FIG. 3 is a flow chart depicting an example of a processing flow upon displaying a reconstructed image.

Steps until the biological information imaging apparatus according to the present embodiment outputs the reconstructed image, will be described with reference to the flow chart in FIG. 3.

Figure 2:
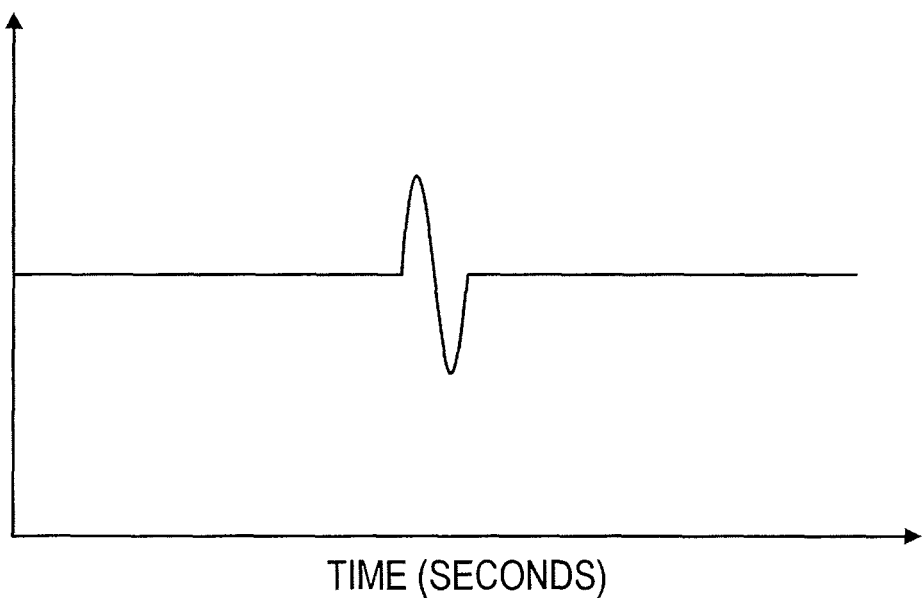
FIG. 2 is a graph depicting an example of an acoustic wave signal.

In S301, pulsed light 2 is irradiated from the light source 4 onto the surface of a biological tissue 1. In S302, the acoustic wave detector 9 detects acoustic waves generated from the light absorber in the biological tissue 1. Normally an acoustic wave generated from a spherical light absorber presents an N-shaped waveform, as shown in FIG. 2, where the abscissa is time and the ordinate is the intensity of the acoustic wave. In S303, the signal processing unit 6 estimates a position of the absorber (distribution of acoustic wave sources) by the iteration method based on the signals (acoustic wave signals: measured signals) obtained by the acoustic wave detector 9, and generates (reconstructs) an image. In S304, the image display unit 5 outputs (displays) the image generated by the signal processing unit 6.

(How to Estimate Distribution of Acoustic Wave Sources)

Now a method for estimating a distribution of acoustic wave sources by the signal processing unit 6 will be described. Here in order to simplify description, a case of estimating distribution of a two-dimensional acoustic wave sources (a case of reconstructing a two-dimensional image) will be described, but the same concept can be applied to the case of estimating a three-dimensional acoustic wave sources (a case of reconstructing a three-dimensional image) as well. Generally processing by the signal processing unit 6 is implemented by a processing unit of a computer executing software (programs).

The present embodiment is based on the concept that the acoustic wave generated from each image element-sized acoustic wave source is unique to the biological tissue, and an acoustic waves generated in an arbitrary acoustic wave source distribution can be represented by the superposition of acoustic waves generated by each acoustic wave source (linearity of acoustic wave). Thereby the acoustic wave source distribution can be estimated from the measured data (acoustic wave signals: measured signals) as an inverse problem. In concrete terms, according to the present embodiment, the estimating unit assumes a distribution of acoustic wave sources, obtains signals corresponding to the position of each acoustic wave source in this assumed distribution from the information stored in the memory unit, and superposes the obtained signals. And the distribution of the acoustic wave sources of which degree of coincidence of the superposed signals and the signals obtained in the actual measurement is the highest, is defined as the distribution of the acoustic wave sources in the biological tissue. In the present embodiment, both a "pixel", which is an element of a two-dimensional reconstructed image, and a "voxel" which is an element of a three-dimensional reconstructed image are collectively called an "image element".

Figure 4:
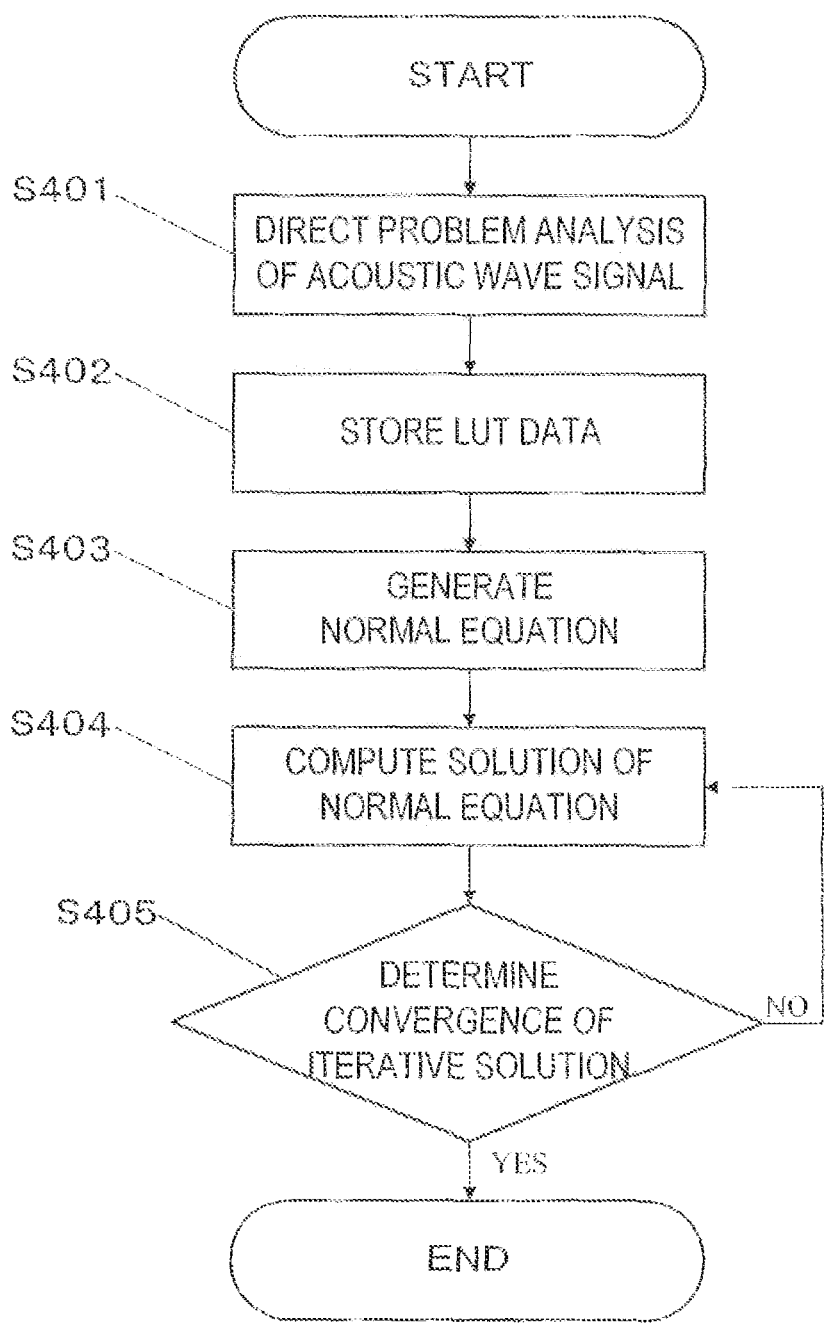
FIG. 4 is a flow chart depicting an example of a processing flow by a signal processing unit.

FIG. 4 is a flow chart depicting an example of processing flow by the signal processing unit 6 according to the present embodiment.

In S401, the signal processing unit 6 (information generation unit) assumes that an acoustic wave source exists in each image element position, and calculates the acoustic wave signal that could be measured in each receiving element by direct problem analysis. In S402, the signal processing unit 6 (memory unit) stores the calculation result in S401 as the array data (LUT (Look Up Table) data: Jacobian sub-matrix).

In direct problem analysis, the acoustic wave signal which could be measured by each receiving element is computed by calculating the solution of the wave equation in Expression 1. In Expression 1, p(x, y, t) means the pressure (acoustic wave) which could be observed in a position (x, y) at time t. c is a sound velocity. The acoustic wave signal may be calculated using an analytic expression, or may be calculated by simulation analysis using an FDM (Finite Difference Method) and an FEM (Finite Element Method).

[Expression 1]

$$\nabla^2 p(x, y, t) - \frac{1}{c^2} \frac{\partial^2}{\partial t^2} p(x, y, t) = 0 \qquad (1)$$

This direct problem analysis may also be executed considering the size of the receiving element (element size), the frequency band of the acoustic wave received by the receiving element, the directivity of the receiving element, and the sound velocity distribution from the acoustic wave source to the receiving element or the like. For example, in numeric analysis, the intensities of acoustic waves that reach a plurality of points in the receiving plane of the receiving element used for the actual measurement (in the plane where the acoustic waves are received) are calculated, and the average value of the intensities is defined as the intensity of the acoustic wave that reaches the receiving element. In numerical analysis, the frequency bands of the acoustic waves received by a plurality of receiving elements can be limited to the frequency bands of the acoustic waves that can be received by the receiving element used for actual measurement. In concrete terms, the calculated acoustic wave signals are Fourier-transformed, and are limited to the frequency bands that can be received by the receiving element used for actual measurement in the frequency space by filter processing, then inverse-Fourier-transform is performed. In numerical analysis, a model in which the sound velocity distribution from each acoustic wave source to the receiving element in the actual measurement is assumed (e.g. sound velocity distribution considering the biological tissue and pressing plate) can be used.

Figure 5A:
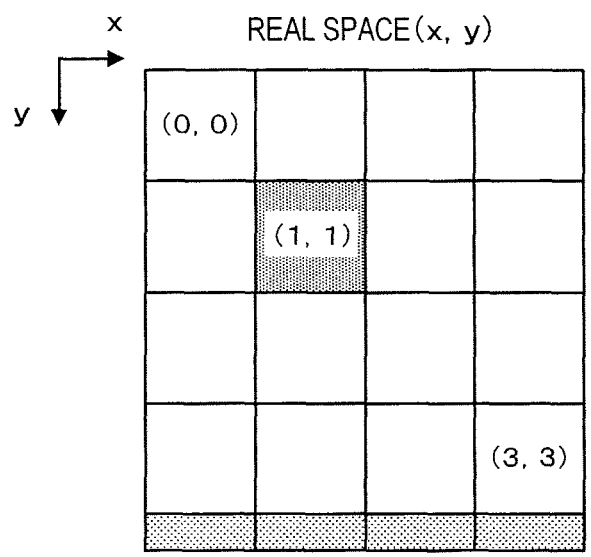
FIG. 5A and FIG. 5B are diagrams depicting an example of LUT data.
Figure 5B:
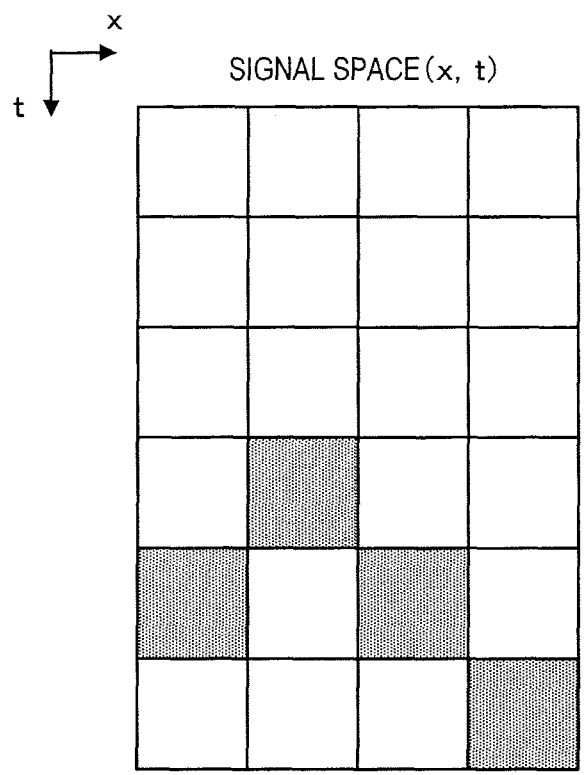

FIG. 5 shows an example of the LUT data in the case of reconstructing a 4 image element×4 image element sized image. FIG. 5A is a diagram depicting inside a biological tissue (real space (x, y)), and FIG. 5B is a diagram depicting an example of an acoustic wave signal obtained by each receiving element (signal space (x, t): space constituted by a position of the receiving element and a receiving time). In FIG. 5, the position filled in black in the real space is a position where an acoustic wave source exists, and a position filled in black (element of a Jacobian sub-matrix) in the signal space is a position (element) which has a value.

In S401, an acoustic wave signal shown in FIG. 5B is calculated as an acoustic wave signal when the acoustic wave exists in the real space coordinates (1, 1), for example. The acoustic wave spreads as a spherical wave as time elapses, so the locus of the acoustic wave signal forms a quadratic curve in the signal space. In the case of reconstructing a 4 image element×4 image element sized image, 4×4=16 of correspondence relationships between the real space coordinates (image element positions) and the acoustic wave signals are obtained.

In S403, the signal processing unit 6 (estimating unit) generates the constituents of the equation used for reconstructing an image (estimating acoustic wave source distribution) based on the LUT data stored in S402.

FIG. 6 shows the equation used for estimating the acoustic wave source distribution which is expressed in matrix format. FIG. 6A is an array of acoustic wave signals for each image element position calculated in S401 (hereafter called "matrix J (Jacobian matrix)"). FIG. 6B shows the acoustic wave source distribution to be estimated (hereafter called "acoustic wave source distribution $\Delta P_I$"). FIG. 6C shows an actually measured value of an acoustic wave signal (hereafter called "acoustic wave signal $\Delta P_m$"). Because of the linearity of the acoustic wave, the acoustic wave signal measured in the case of the acoustic wave source distribution, $\Delta P_I$ is a product $J\Delta P_I$ of the acoustic wave signal for each image element position (matrix J), and the acoustic wave source distribution $\Delta P_I$. Therefore if a correct acoustic wave source distribution $\Delta P_I$ is estimated, the values $J\Delta P_I$ and $\Delta P_m$ perfectly match or are close to each other. This is represented as shown in Expression 2.

[Expression 2]

$$J\Delta P_I \approx \Delta P_m \quad (2)$$

Here matrix J is normally not a square matrix, but becomes like Expression 3 if both sides are multiplied by $J^T$ (transposed matrix of J). This is called a "normal equation".

[Expression 3]

$$J^T J \Delta P_I = J^T \Delta P_m \quad (3)$$

In S404, the signal processing unit 6 (estimating unit) determines the solution of the normal equation (Expression 3).

To solve the normal equation, a conventional method to solve simultaneous linear equations (direct solution iterative solution) can be used. If the size of the area for which the acoustic wave source distribution is estimated is large, as in the case of generating a three-dimensional image as a reconstructed image, it is preferable to use an iterative solution, such as a conjugate gradient method (in this example, it is assumed that the iterative solution is used). The solution of the normal equation (Expression 3) is a least square solution which minimizes

[Expression 4]

$$\|J\Delta P_I - \Delta P_m\|^2 \quad (4)$$

In other words, the solution of the normal equation (Expression 3) is an optimum solution which satisfies (Expression 2) as a least square solution. Thereby the acoustic wave source distribution $\Delta P_I$, for obtaining the acoustic wave signals of which degree of coincidence with actually measured acoustic wave signals is the highest, can be estimated.

In S405, the signal processing unit 6 (estimating unit) evaluates the value obtained by Expression 4 (determines convergence of the iterative solution). In concrete terms, it is determined whether the value obtained by Expression 4 is a predetermined threshold (e.g. $\epsilon$=1.0e−6) or less. The processing in S404 is repeated until this value becomes the predetermined threshold or less.

If noise exists in the obtained acoustic wave signal,

[Expression 5]

$$(J^T J + \alpha I)\Delta P_I = J^T \Delta P_m \quad (5)$$

can be solved, where a predetermined value α is added to the diagonal element at the left hand side of Expression 3. In this case, it is guaranteed that the solution is a least square solution that minimizes

[Expression 6]

$$\|J\Delta P_I - \Delta P_m\|^2 + \alpha \|\Delta P_I\|^2 \quad (6)$$

By the above processing, the acoustic wave source distribution $\Delta P_I$ can be estimated based on a matrix J, which is provided in advance, and actually measured values (acoustic wave signals $\Delta P_m$), and an image can be reconstructed.

If the size of the reconstructed image is large (if the area of acoustic wave source distribution to be estimated is large, e.g. the case of reconstructing a large sized two-dimensional or three-dimensional image), it is difficult to store the entire matrix in the memory, as seen in FIG. 6A, considering practical memory capacity. So the present inventors invented a method for implementing a dramatic saving of memory using the later mentioned symmetry. The present inventors also invented a method for increasing the speed of computing using the localization of matrix elements. Thereby a large sized reconstructed image can be generated even with a standard PC (even if the memory capacity and computing capability are limited).

(Memory Saving)

First memory saving (how to compress information to be stored in the memory unit) will be described.

It is assumed that a first signal is a signal which is output from a plurality of receiving elements when an acoustic wave source exists in a first position among a plurality of predetermined positions, and a second signal is a signal which is output from the plurality of receiving elements when an acoustic wave source exists in a second position. In this case, the first signal and second signal may have portions which coincide with each other by parallel displacement or rotary displacement in a signal space (this property is called "symmetry"). According to this present embodiment, the coinciding portions of the first signal and the second signal are commonly used, so that the data volume of the information to be stored in memory unit is compressed.

Figure 7:
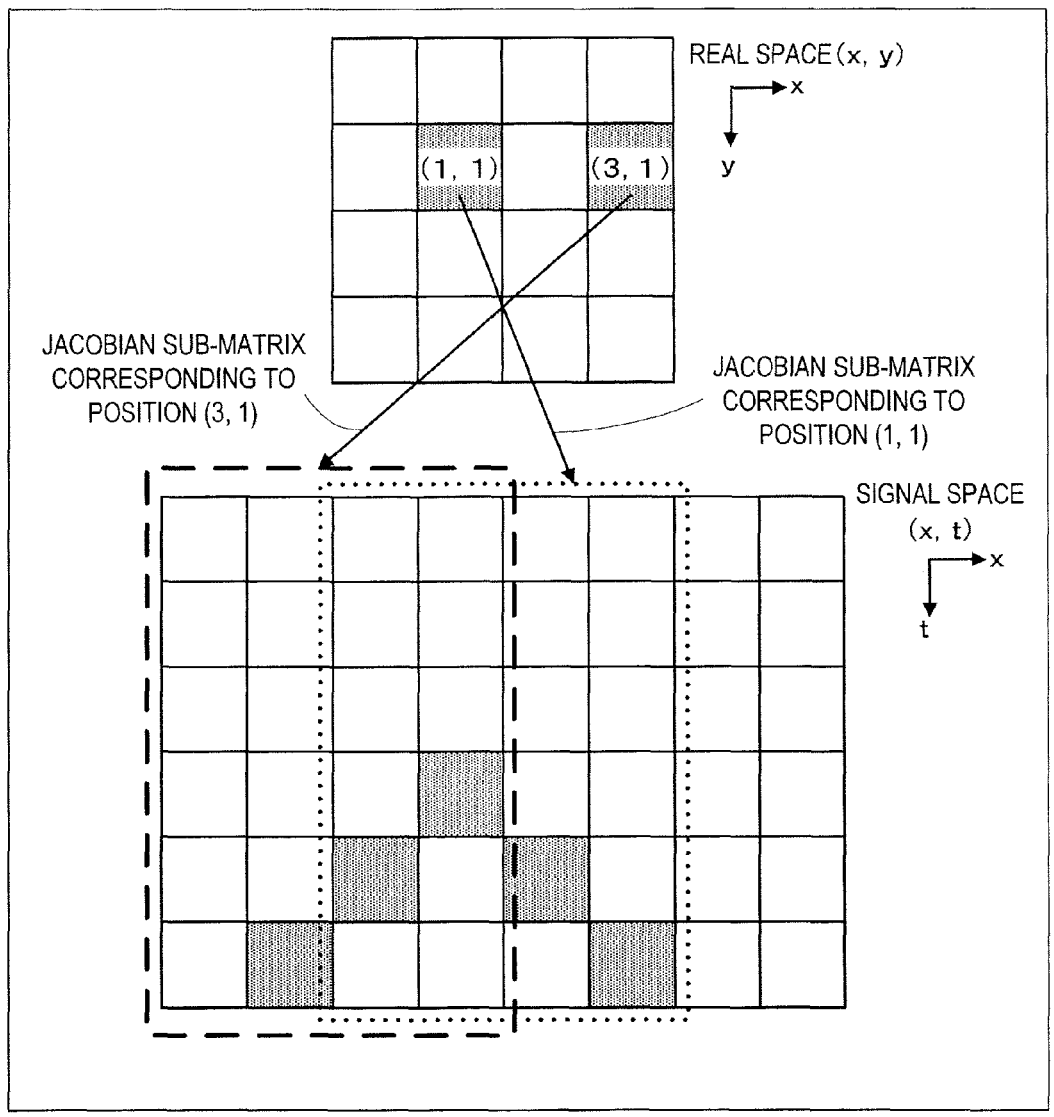
FIG. 7 is a diagram depicting an example of a method for saving memory.

FIG. 7 is a diagram depicting an example of a method for saving memory. In the method in FIG. 7, LUT data, larger than the above mentioned LUT data for each image element position (LUT data double the size of FIG. 5B in the case of the example in FIG. 7), is used. And using the above mentioned symmetry, the area in the LUT data to be referred to is changed for each image element position disposed in the array direction (x direction in FIG. 7) of the receiving elements. As a result, a number of LUT data can be decreased, and memory can be saved.

Figure 8:
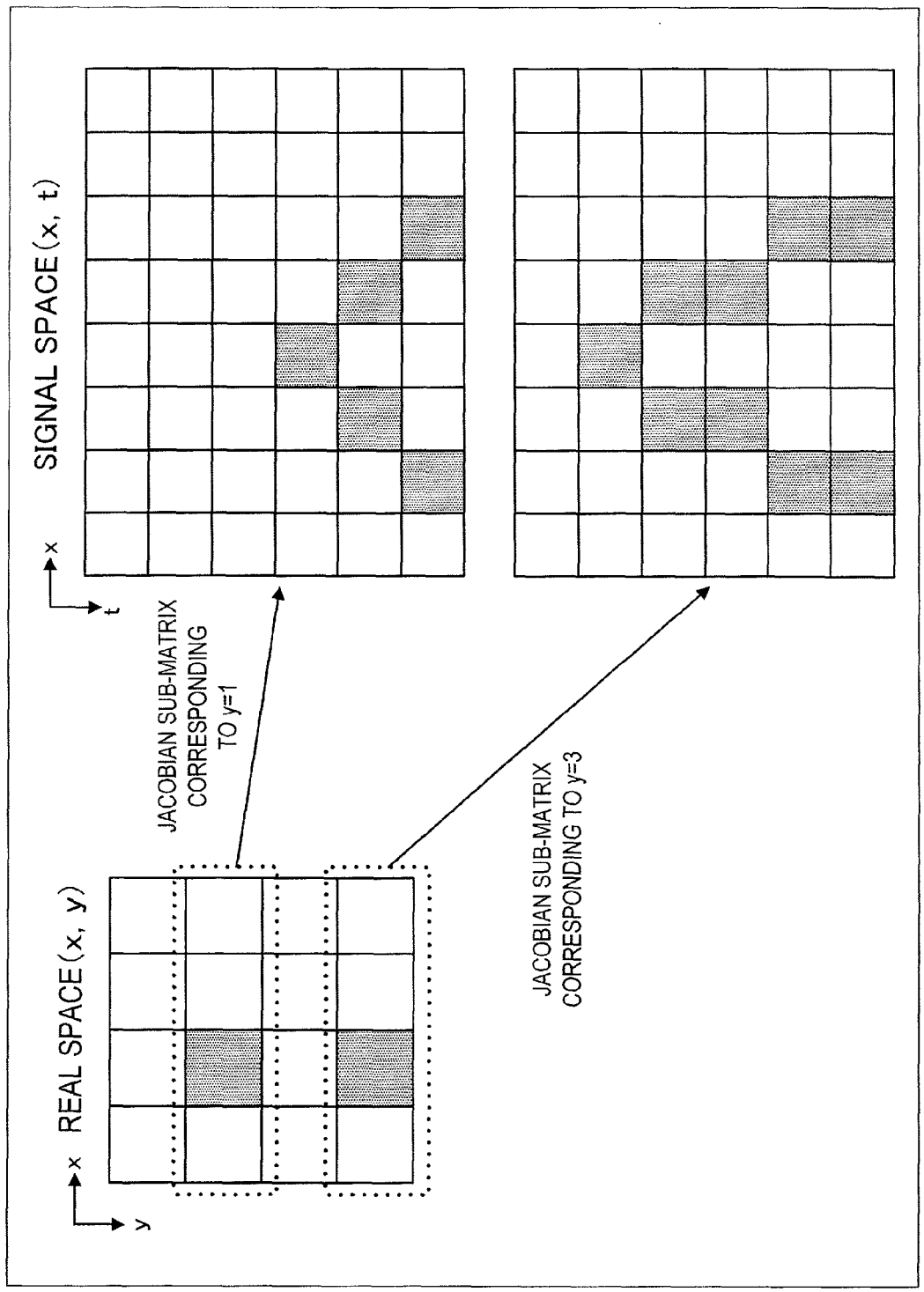
FIG. 8 is a diagram depicting an example of a Jacobian sub-matrix.

However in the acoustic wave signal, when the acoustic wave source is an image element position of which distance to a receiving element is different, as shown in FIG. 8, the curvature of locus of the acoustic wave is different in signal space respectively. Therefore a plurality of Jacobian sub-matrixes, of which distances to the plurality of receiving elements are different from one another (Jacobian sub-matrixes for each position in the y direction (depth direction) in FIG. 8), are required.

Figure 9:
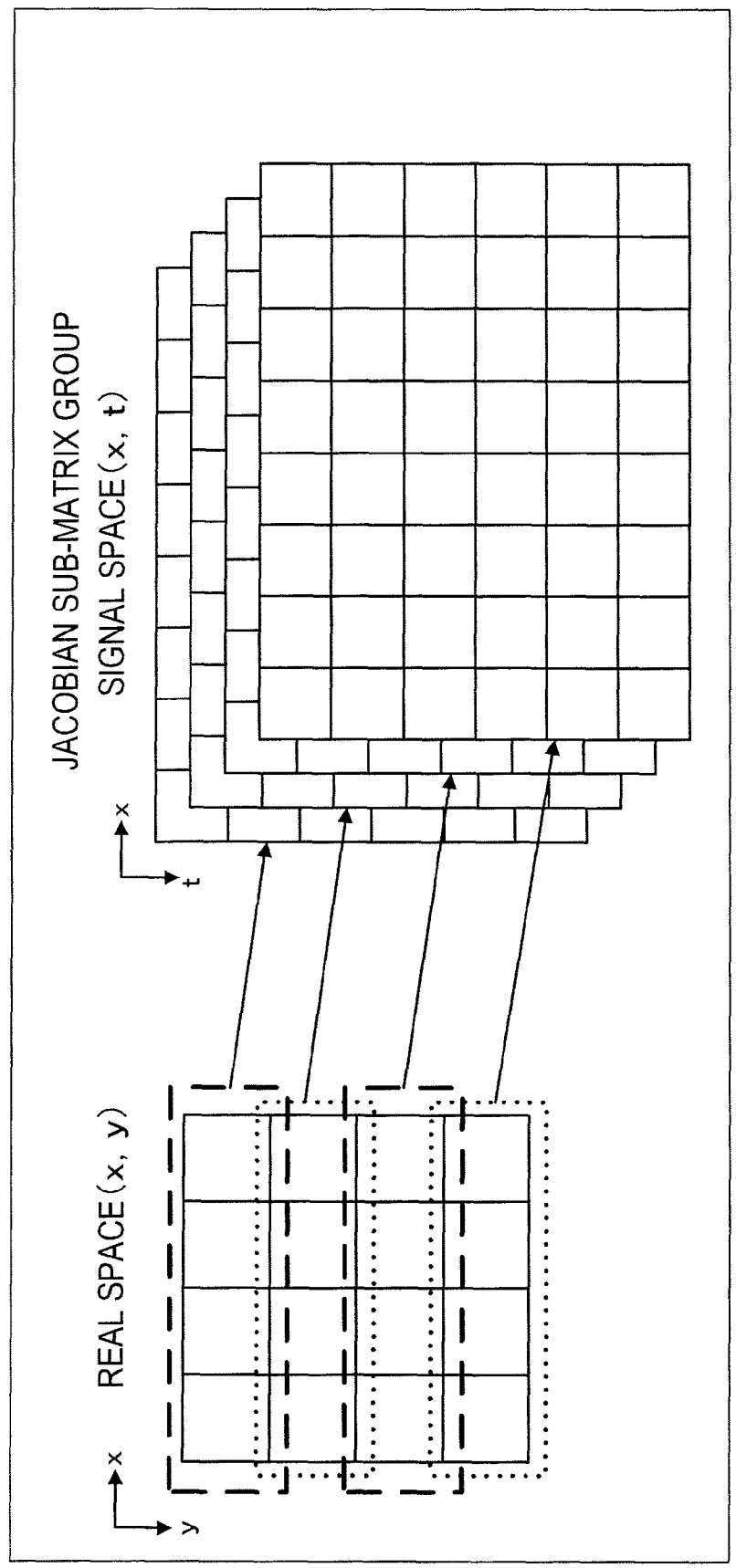
FIG. 9 is a diagram depicting an example of a Jacobian sub-matrix group provided by using symmetry.

FIG. 9 is a diagram depicting an example of a Jacobian sub-matrix group (Jacobian sub-matrix group prepared using the above mentioned symmetry) which is used for the case of reconstructing a 4 image element×4 image element two-dimensional image. In FIG. 9, a value in each element in the Jacobian sub-matrix is omitted.

In the case of FIG. 6A, a total number of elements of the Jacobian sub-matrix group is 4 (number of receiving elements)×6 (number of times of sampling)×16 (number of image elements of reconstructed image)=384. In the case of the example in FIG. 9, on the other hand, only 2×4 (number of receiving elements)×6 (number of times of sampling)×4 (number of image elements in depth direction)=192 elements are sufficient. Therefore compared with the case of FIG. 6A, the required memory size in the case of FIG. 9 can be ½. This memory saving effect becomes obvious when the size of the area for which the acoustic wave source distribution is estimated is large. For example, in the case of generating a 64 image element×64 image element reconstructed image, the use of symmetry can decrease the required memory size to be 1/32 of the case of using a Jacobian sub-matrix for each image element position.

Figure 10:
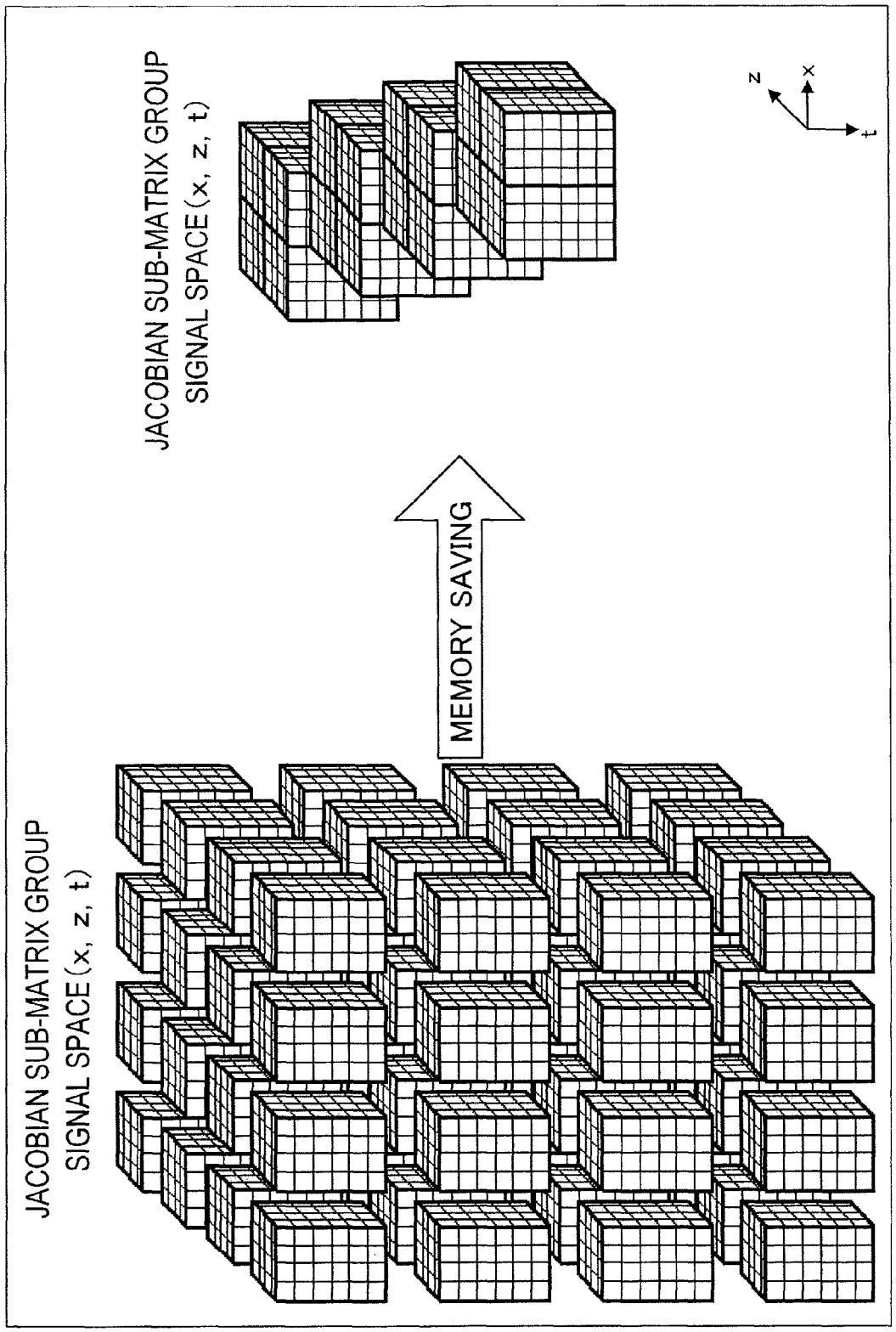
FIG. 10 is a diagram depicting an example of a Jacobian sub-matrix group provided by using symmetry.

FIG. 10 is a diagram depicting an example of a Jacobian sub-matrix group (Jacobian sub-matrix group prepared using the above mentioned symmetry), which is used for the case of reconstructing a 4 image element×4 image element×4 image element three-dimensional image. FIG. 10 is an example when a number of times of samplings is 6 using 16 receiving elements, which correspond to one surface (4 image element×4 image element) three-dimensional image. In FIG. 10, a value in each element in the Jacobian sub-matrix is omitted, just like FIG. 9.

As FIG. 10 shows, the total number of elements (required memory size) of the Jacobian sub-matrix group is smaller in the case of using the Jacobian sub-matrix utilizing symmetry, than the case of using a Jacobian sub-matrix for each image element position. For example, in the case of generating a 64 image element×64 image element×64 image element reconstructed image, the required memory size can be 1/1024 by utilizing the above mentioned symmetry, compared with the case of using a Jacobian sub-matrix for each image element position. As a result, acoustic wave source distribution can be estimated for a size of an area which could not be implemented by prior art.

In this way, this memory saving effect becomes more obvious as the size of the area for which the acoustic wave source distribution is estimated is larger, and becomes even more obvious especially when three-dimensional acoustic wave source distribution is estimated.

(Increasing Processing Speed)

The increase of processing speed will now be described.

Figure 11:
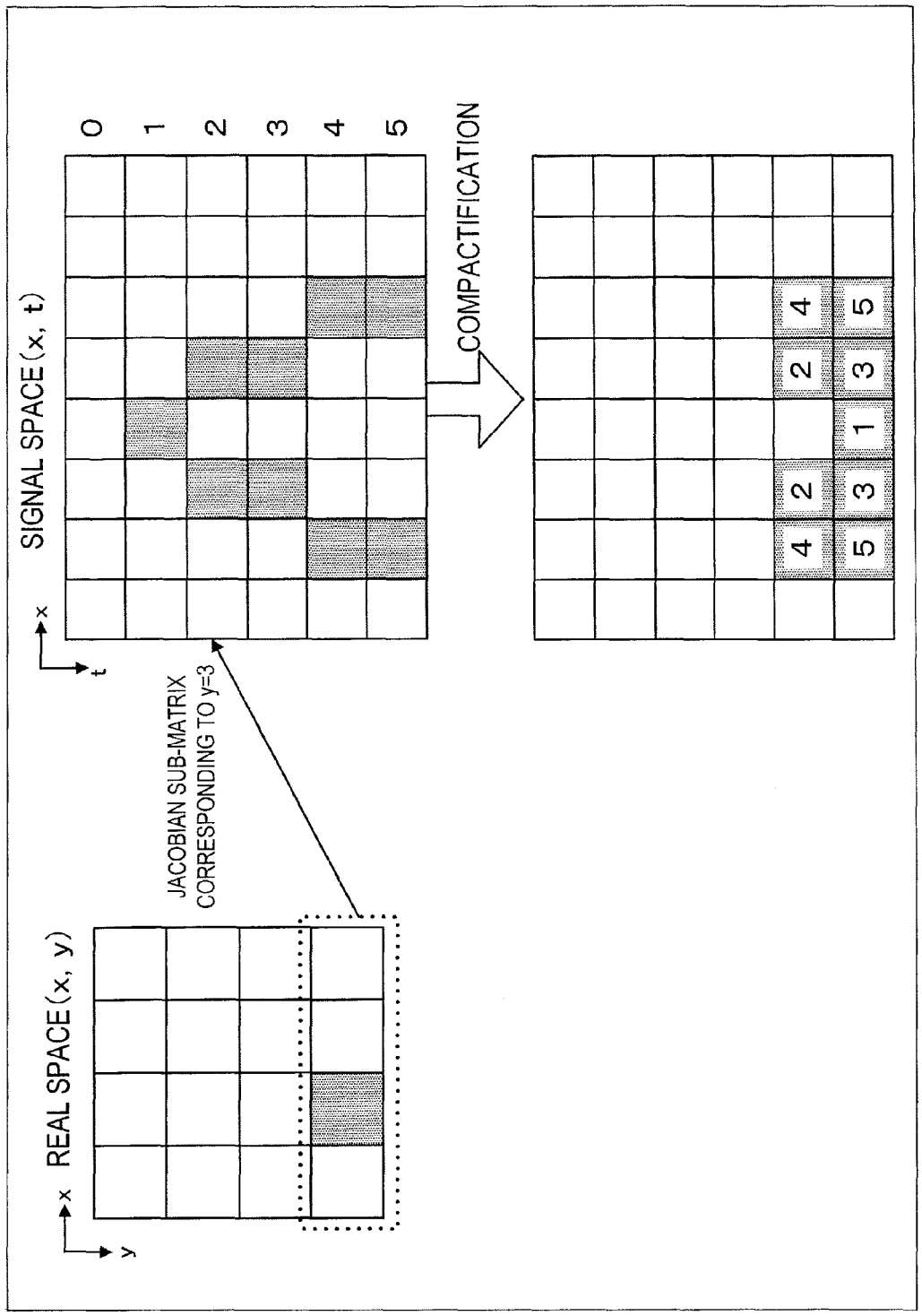
FIG. 11 is a diagram depicting an example of a method for increasing processing speed.

FIG. 11 is a diagram depicting an example of a method for increasing speed of computing (processing) (numerical values 0 to 5 in FIG. 11 are values of t). Since an acoustic wave detected by the receiving element is a pulsed wave, most elements of the Jacobian sub-matrix virtually have no values. Therefore in the present embodiment, computing speed is increased by compressing (omitting) the areas which have no values. In concrete terms, as information to be stored in the memory unit, information to represent a combination of a receiving element, which receives an acoustic wave when an acoustic wave source is assumed to exist in the position, and a reception time thereof (position in the Jacobian sub-matrix) is used for each of a plurality of predetermined positions. This compression of Jacobian sub-matrix is called "compactification".

Figure 12:
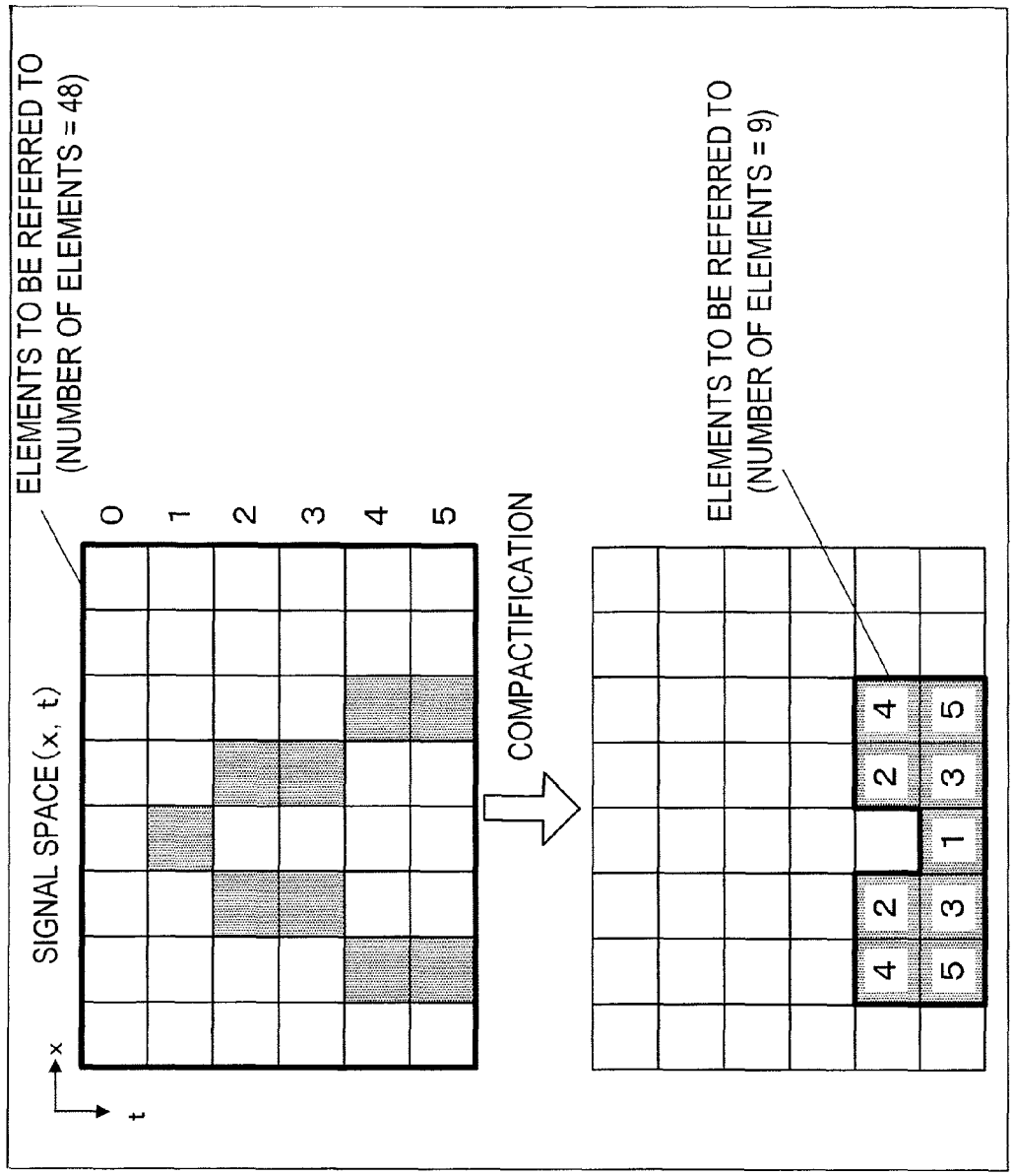
FIG. 12 is a diagram depicting an effect of increasing processing speed by compactification.

FIG. 12 is a diagram depicting an effect of increasing processing speed by compactification of a Jacobian sub-matrix. In the example in FIG. 12, the Jacobian sub-matrix before compactification has 8×6 elements. Therefore if this Jacobian sub-matrix is used, a number of elements to be referred to is 48. In the case of the Jacobian sub-matrix after compactification, on the other hand, only elements having values are referred to, so a number of elements to be referred to is 9. Thereby a computing volume to refer to elements of a Jacobian sub-matrix can be decreased to 9/48, and processing speed can be increased.

If elements of the Jacobian sub-matrix are rearranged in the sequence of greater value, then only values having a predetermined value or more are referred to in the sequence of greater value when restoring elements, and accuracy drops but computing volume can be decreased even more (processing speed can be increased).

FIG. 13 are diagrams depicting examples of an array pattern of receiving elements and an obtained reconstructed image. FIG. 13A shows an example of reconstructing a three-dimensional image (estimating three-dimensional acoustic wave source distribution) based on data measured by a plurality of receiving elements arrayed two-dimensionally. FIG. 13B shows an example of reconstructing a two-dimensional image (estimating two-dimensional acoustic wave source distribution) based on the data measured by a plurality of receiving elements arrayed two-dimensionally. FIG. 13C shows an example of reconstructing a two-dimensional image (estimating a two-dimensional acoustic wave source distribution) based on the data measured by a plurality of receiving elements arrayed one-dimensionally.

If the above method utilizing symmetry is used, a memory saving effect can be obtained in any case of FIG. 13A to FIG. 13C. The memory saving effect is particularly high in the case of FIG. 13A. In the examples in FIG. 13, a plurality of receiving elements are disposed on one surface of a cube, but a plurality of receiving elements may be disposed on a plurality of surfaces of a cube.

In the present embodiment, the information to be stored in the memory unit is generated by numerical analysis, but such information may also be generated by using the measured values of an acoustic waves which are actually measured by a specimen simulating a biological tissue. In concrete terms, a specimen for simulating the sound velocity inside biological tissue and the sound velocity of the pressing plate is fabricated, and an acoustic wave source corresponding to the size of the unit image element is disposed. A Jacobian sub-matrix may be generated by measuring the acoustic waves (acoustic waves generated from the disposed acoustic wave source) using this specimen.

In the configuration of the present embodiment, the signal processing unit 6 has an information generation unit for generating information to be stored in the memory unit, but the information generated in another apparatus may be stored in the memory unit.

The present embodiment is a case where the symmetry is translational symmetry (the array directions of the receiving element are linear), but even in cases of axial symmetry or spherical symmetry, memory saving can be implemented utilizing these symmetric properties. In the case of axial symmetry or spherical symmetry, however, information on the position and shape of the receiving element and correspondence with the signal to be measured is required.

Example 1

The result of reconstructing an image (estimating an acoustic wave source distribution) by simulation will now be described with reference to FIG. 14.

In this example, a 64 image element×64 image element reconstructed image is generated. In each image in FIG. 14, it is assumed that the coordinates of the upper left corner are (0, 0), and the coordinates of the lower right corner are (63, 63).

Figure 14C:
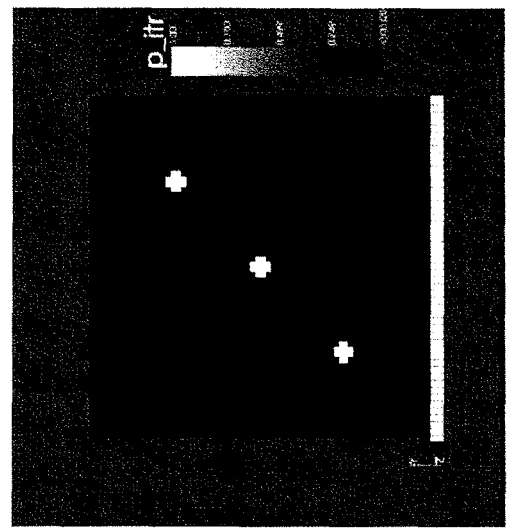
FIG. 14A, FIG. 14B and FIG. 14C show examples of the result of estimating an acoustic wave source distribution by simulation.
Figure 14B:
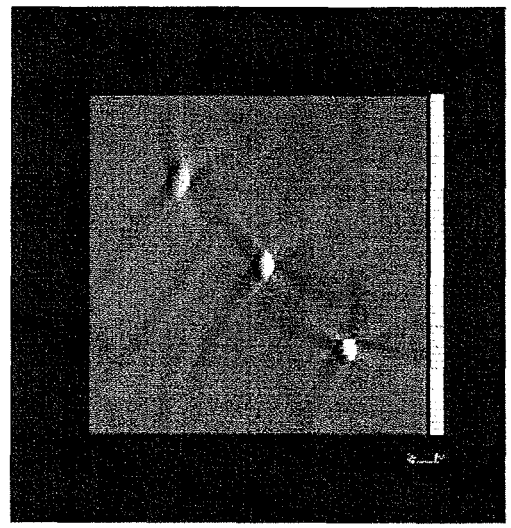
Figure 14A:
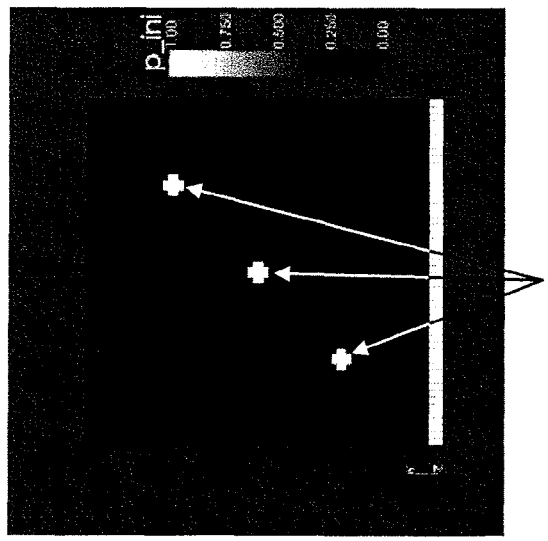

FIG. 14A shows an acoustic wave source distribution for generating data of measured values (acoustic wave signal $\Delta P_m$). In this example, an acoustic wave source is set in coordinates (15, 15), (31, 31) and (47, 47) respectively. Receiving elements are disposed only on one side (bottom side) out of the four sides. The number of receiving elements is 64. To generate data on measured values (acoustic wave signal $\Delta P_m$), a number of times of samplings is 256.

FIG. 14B shows a reconstructed image obtained from the data on the measured values (acoustic wave signal $\Delta P_m$) based on a conventional back projection method. As FIG. 14B shows, in the case of a conventional back projection method, the clear artifact is observed, and the original acoustic wave source distribution cannot be estimated correctly. The contrast of the image is low and unclear. This is because the receiving elements, which receive signals, do not exist in all the directions around the subject (NPL 1).

FIG. 14C shows a reconstructed image obtained by the method of the present invention (use of the direct problem analysis result, memory saving utilizing symmetry, and compactification of the Jacobian sub-matrix). As FIG. 14C shows, according to this example, which uses the direct problem analysis result which is provided in advance, accurate acoustic wave source distribution can be estimated even if receiving elements do not exist in all the directions around the subject, compared with the case of using a conventional back projection method (FIG. 14B).

With a conventional iteration method, the size of the area where the acoustic wave source distribution can be accurately estimated, as shown in FIG. 14C, is considerably limited because of the memory capacity and computing speed.

For example, if an acoustic wave source distribution is computed based on a conventional iteration method using a standard PC, it takes 10 minutes of computing time. In the case of the present example, on the other hand, it only takes about 5 seconds of computing time (about 1/120 of prior art) if a similar PC is used, since the Jacobian sub-matrix is compact.

Also in the case of the present example, memory capacity to be used can be reduced to 1/32 compared with the case of using a Jacobian sub-matrix for each image element position, since a Jacobian sub-matrix utilizing symmetry is used.

As the above results show, the present invention contributes dramatically to the practicality of diagnostic apparatuses.

Example 2

The effect of memory saving is verified by generating a 64 image element×64 image element×64 image element of a reconstructed image. In this example, 4096 receiving elements, which correspond to one surface (64 image element×64 image element) three-dimensional image are used, and a number of times of sampling performed is 512.

In this case, the memory capacity required when symmetry is not utilized is in proportion to the total number of elements of the Jacobian sub-matrix group, that is 64² (number of receiving elements)×512 (number of times of sampling)×64³ (number of image elements). The memory capacity required for the case of utilizing symmetry, on the other hand, is in proportion to 4×64² (number of receiving elements)×512 (number of times of sampling)×64 (number of image elements in depth direction). In other words, according to this example, which utilizes symmetry, the same computing can be performed with a memory capacity that is 1/1024 of the memory capacity in the case of not utilizing symmetry.

Example 3

The effect of compactification of the Jacobian sub-matrix on increasing the processing speed is verified by generating a 64 image element×64 image element×64 image element of a reconstructed image. In this example, 4096 receiving elements, which correspond to one surface (64 image pixels×64 image pixels) of a three-dimensional image are used, and a number of times of sampling is 512.

In this case, because of compactification of the Jacobian sub-matrix, a number of elements to be referred to in the Jacobian sub-matrix reduces from 4×(64×64×512) to 4×(64×64×30). In other words, compared with the case before compactification, a number of elements to be referred to become 30/512. As a result, even if processing required for compactification of the Jacobian sub-matrix is added, the overall processing speed can be about 15 times faster.

As described above, according to the biological information obtaining apparatus and the biological information obtaining method of the present embodiment, accurate distribution of acoustic wave sources can be estimated by a simple method utilizing the property where the acoustic wave generated from each acoustic wave source is unique to the biological tissue and the linearity property of the acoustic wave. In concrete terms, the distribution of the acoustic wave sources is assumed, and signals corresponding to the positions of the acoustic wave sources in this distribution are superposed. And the distribution of the acoustic wave sources, in which the degree of coincidence between the superposed signals and signals obtained in the actual measurement is highest, is defined as the distribution of the acoustic wave sources in the biological tissue. Thereby accurate distribution of the acoustic wave sources can be estimated. Also signals corresponding to a plurality of predetermined positions are stored, and signals obtained in the actual measurement are represented by superposition of these stored signals. Therefore unlike prior art, it is not necessary to calculate acoustic waves using an analysis solution each time iterative calculation is performed, therefore the distribution of the acoustic wave sources can be easily estimated.

Aspects of the present invention can also be realized by a computer of a system or apparatus (or devices such as a CPU or MPU) that reads out and executes a program recorded on a memory device to perform the functions of the above-described embodiment(s), and by a method, the steps of which are performed by a computer of a system or apparatus by, for example, reading out and executing a program recorded on a memory device to perform the functions of the above-described embodiment(s). For this purpose, the program is provided to the computer for example via a network or from a recording medium of various types serving as the memory device (e.g., non-transitory computer-readable medium).

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

This application claims the benefit of Japanese Patent Application No. 2010-008366, filed on Jan. 18, 2010, which is hereby incorporated by reference herein its entirety.

What is claimed is:

1. A subject information obtaining apparatus, comprising:
a receiver configured to receive an acoustic wave generated from a subject by irradiation of light at a plurality of receiving positions, and output actual signals;
a memory configured to store information on assumed signals for each of a plurality of predetermined positions within the subject, each of the assumed signals being a signal that is assumed to be received by said receiver in a case in which acoustic wave source exists at a predetermined position within the subject; and
an estimator configured to estimate an actual distribution of acoustic wave sources within the subject by an iteration method based on the information stored in said memory and the actual signals,
wherein a coinciding portion of the information representing a first assumed signal for a first predetermined position within the subject and the information representing a second assumed signal for a second predetermined position within the subject is commonly stored in said memory as a common piece of information, in a case in which the first and second assumed signal have symmetry, and
wherein said estimator is configured to
obtain an assumed distribution of assumed acoustic wave sources,
obtain assumed signals corresponding to the plurality of predetermined positions of respective assumed acoustic wave sources in the assumed distribution from the information stored in said memory, and
obtain a distribution of acoustic wave sources, of which degree of coincidence between the assumed signals and the actual signals is highest, as the actual distribution of the actual acoustic wave sources within the subject.

2. The subject information obtaining apparatus according to claim 1, wherein said memory is configured to store, for each of the plurality of predetermined positions within the subject, the information representing a combination of the receiving position of an acoustic wave when an acoustic wave source is assumed to exist at a predetermined position within the subject and a receiving time of the acoustic wave at the receiving position.

3. The subject information obtaining apparatus according to claim 1, further comprising a generator configured to generate information to be stored in said memory by numerical analysis.

4. The subject information obtaining apparatus according to claim 3, wherein
said receiver includes a plurality of receiving elements configured to receive an acoustic wave generated from the subject by irradiation of light, and
said generator is configured to calculate, in the numerical analysis, intensities of an acoustic wave that reach a plurality of points on a receiving surface of said receiving element used for an actual measurement, and defines an average value of the intensities as an intensity of an acoustic wave reaches this receiving element.

5. The subject information obtaining apparatus according to claim 3, wherein
said receiver includes a plurality of receiving elements configured to receive an acoustic waves generated from the subject by irradiation of light, and
said generator is configured to limit, in the numerical analysis, frequency bands of the acoustic waves, received by said plurality of receiving elements, to frequency bands of the acoustic waves that can be received by said plurality of receiving elements used for an actual measurement.

6. The subject information obtaining apparatus according to claim 3, wherein said generator is configured to use, in the numerical analysis, a model in which a sound velocity distribution from the acoustic wave source to a receiving position in an actual measurement is assumed.

7. The subject information obtaining apparatus according to claim 1, wherein said receiver includes a plurality of receiving elements configured to receive an acoustic wave generated from the subject by irradiation of light.

8. The subject information obtaining apparatus according to claim 1, wherein the coinciding portion of the information representing the first assumed signal and the information representing the second assumed signal is commonly stored in said memory as the common piece of information, in a case in which the first and second assumed signal have a coinciding portion by parallel displacement or rotary displacement in a signal space.

9. The subject information obtaining apparatus according to claim 8, wherein the signal space includes a position of the plurality of receiving elements and a time that the plurality of receiving elements receive an acoustic wave.

10. A subject information obtaining apparatus, comprising:
a receiver configured to receive an acoustic wave generated from a subject by irradiation of light at a plurality of receiving positions, and output actual signals;
a memory configured to store information on assumed signals for each of a plurality of predetermined positions within the subject, each of the assumed signals being a signal that is assumed to be received by said receiver in a case in which acoustic wave source exists at a predetermined position within the subject; and
an estimator configured to estimate an actual distribution of acoustic wave sources within the subject by an iteration method based on the information stored in said memory and the actual signals outputted from said receiver,
wherein a coinciding portion of the information representing a first assumed signal for a first predetermined position within the subject and the information representing a second assumed signal for a second predetermined position within the subject is commonly stored in said memory as a common piece of information, in a case in which the first and second assumed signal have symmetry, and wherein said estimator is configured to
obtain an assumed distribution of assumed acoustic wave sources,
obtain assumed signals corresponding to the plurality of predetermined positions of respective assumed acoustic wave sources in the assumed distribution from the information stored in said memory, and
obtain a distribution of acoustic wave sources, of which an error of a difference between the assumed signals and the actual signals is minimized, as the actual distribution of the actual acoustic wave sources within the subject.

11. The subject information obtaining apparatus according to claim 10, wherein said estimator is configured to obtain the distribution of acoustic wave sources, of which the error is a predetermined threshold or less.

12. The subject information obtaining apparatus according to claim 10, wherein said estimator is configured to obtain the error by calculating residual sum of squares between the assumed signals and the actual signals.

13. The subject information obtaining apparatus according to claim 10, wherein the coinciding portion of the information representing the first assumed signal and the information representing the second assumed signal is commonly stored in said memory as the common piece of information, in a case in which the first and second assumed signal have the coinciding portion by parallel displacement or rotary displacement in a signal space.

14. The subject information obtaining apparatus according to claim 10, further comprising a generator configured to generate information to be stored in said memory by numerical analysis, wherein
said receiver includes a plurality of receiving elements configured to receive an acoustic wave generated from the subject by irradiation of light, and
said generator is configured to, in the numerical analysis, calculate intensities of an acoustic wave that reach a plurality of points on a receiving surface of said receiving element used for the actual measurement, and
define an average value of the intensities as an intensity of an acoustic wave reaches this receiving element.

15. The subject information obtaining apparatus according to claim 10, further comprising a generator configured to generate information to be stored in said memory by numerical analysis, wherein
said receiver includes a plurality of receiving elements configured to receive an acoustic wave generated from the subject by irradiation of light, and
said generator is configured to, in the numerical analysis, limit frequency bands of the acoustic wave, received by said plurality of receiving elements, to frequency bands of the acoustic wave that can be received by said plurality of receiving elements used for the actual measurement.

16. A subject information obtaining method comprising:
obtaining, by an estimator, actual signals outputted from a receiver by receiving an acoustic wave generated from a subject by irradiation of light at a plurality of receiving positions by a receiver,
obtaining, by the estimator, an assumed distribution of assumed acoustic wave sources from a memory containing the assumed distribution,
obtaining, by the estimator, assumed signals corresponding to a plurality of predetermined positions of respective assumed acoustic wave sources in the assumed distribution from information on assumed signals for each of the plurality of predetermined positions within the subject stored in the memory, each of the assumed signals being a signal that is assumed to be received by the receiver in a case in which an acoustic wave source exists at a predetermined position within the subject; and
obtaining, by the estimator, a distribution of acoustic wave sources within the subject by an iteration method using the actual signals and the assumed signals, of which an error of a difference between the assumed signals and the actual signals is minimized, as an actual distribution of the actual acoustic wave sources within the subject,
wherein a coinciding portion of the information representing a first assumed signal for a first predetermined position within the subject and the information representing a second assumed signal for a second predetermined position within the subject is commonly stored in the memory as a common piece of information, in a case in which the first and second assumed signals have symmetry.

17. The subject information obtaining method according to claim 16, wherein, in said step of obtaining a distribution of acoustic wave sources within the subject, the distribution of acoustic wave sources, of which the error is a predetermined threshold or less, is obtained.

18. The subject information obtaining method according to claim 16, wherein, in said step of obtaining a distribution of acoustic wave sources within the subject, the error is obtained by calculating residual sum of squares between the assumed signals and the actual signals.

19. The subject information obtaining method according to claim 16, wherein the coinciding portion of the information representing the first assumed signal and the information representing the second assumed signal is commonly stored in the memory as the common piece of information, in a case in which the first and second assumed signal have the coinciding portion by parallel displacement or rotary displacement in a signal space.

* * * * *